(12) United States Patent
Maresca, Jr. et al.

(10) Patent No.: US 7,197,914 B2
(45) Date of Patent: Apr. 3, 2007

(54) METHOD AND APPARATUS FOR DETECTING AND LOCATING LEAK HOLES IN A PIPELINE USING TRACERS

(75) Inventors: Joseph W. Maresca, Jr., Sunnyvale, CA (US); Wesley L. Bratton, Richland, WA (US)

(73) Assignee: Vista Engineering Technologies, Kennewick, MA (US)

( * ) Notice: Subject to any disclaimer, the term of this patent is extended or adjusted under 35 U.S.C. 154(b) by 6 days.

(21) Appl. No.: 10/960,407

(22) Filed: Oct. 6, 2004

(65) Prior Publication Data

US 2007/0051165 A1 Mar. 8, 2007

Related U.S. Application Data

(60) Provisional application No. 60/509,316, filed on Oct. 6, 2003, provisional application No. 60/509,312, filed on Oct. 6, 2003.

(51) Int. Cl.
*G01M 3/04* (2006.01)
(52) U.S. Cl. ...................................................... 73/40.7
(58) Field of Classification Search ............... 73/28.01, 73/28.04, 28.05, 28.06, 863.22, 863.23, 40.07
See application file for complete search history.

(56) References Cited

U.S. PATENT DOCUMENTS

| | | | | |
|---|---|---|---|---|
| 3,342,990 A * | 9/1967 | Barrington et al. | ......... | 250/288 |
| 3,425,264 A * | 2/1969 | Frei | ........................ | 73/40.5 R |
| 3,729,983 A * | 5/1973 | Coppens | ...................... | 73/40.7 |
| 3,762,212 A * | 10/1973 | Morley et al. | ................ | 73/40.7 |
| 4,754,638 A * | 7/1988 | Brayman et al. | ............. | 73/40.7 |
| 5,416,323 A * | 5/1995 | Hoots et al. | .................. | 250/302 |
| 5,535,253 A * | 7/1996 | Loisy et al. | ................. | 376/250 |
| 5,681,983 A * | 10/1997 | Seigeot | ........................ | 73/40.7 |
| 5,767,390 A * | 6/1998 | Chapman, IV | ............... | 73/40.7 |
| 5,817,927 A * | 10/1998 | Chen et al. | ................... | 73/40.7 |
| 5,939,619 A * | 8/1999 | Achter et al. | ................. | 73/40.7 |
| 5,939,679 A | 8/1999 | Ollson | | |
| 6,321,595 B1 * | 11/2001 | Pope et al. | ............... | 73/152.39 |
| 6,329,165 B1 * | 12/2001 | Chattoraj et al. | .............. | 435/29 |
| 6,359,645 B1 | 3/2002 | Sivoace | | |
| 6,464,633 B1 | 10/2002 | Hosoda et al. | | |
| 6,730,227 B2 * | 5/2004 | Zeiher et al. | ................ | 210/650 |
| 6,793,699 B2 * | 9/2004 | Coleman et al. | .............. | 48/194 |

* cited by examiner

*Primary Examiner*—Michael Cygan
(74) *Attorney, Agent, or Firm*—David H. Jaffer; Pillsbury Winthrop Shaw Pittman LLP (57) ABSTRACT

A method and an apparatus for finding the location of one or more holes in a fluid flow system such as pipe, duct, or conduit using one or more tracers that interact with or can be chemically or physically differentiated from those of the liquid or gas contents located outside the system and pulled back into the system when the system is placed under a vacuum. The preferred embodiment of this detection and location method uses one or more interactive tracers that are injected into a pipe or duct that may be leaking at one location and then monitor the concentration of these tracers at the same or another location in the pipe or duct. Detection and location are accomplished by analysis of the characteristic features of measured curves of tracer concentration. Various types of interactive tracers may be used, including partitioning and reactive tracer gaseous tracers.

29 Claims, 9 Drawing Sheets

METHOD AND APPARATUS FOR DETECTING AND LOCATING LEAK HOLES IN A PIPELINE USING TRACERS

CROSS-REFERENCE TO RELATED APPLICATIONS

This application claims the benefit of U.S. Provisional Application No. 60/509,316 filed Oct. 6, 2003, and U.S. Provisional Application No. 60/509,312 filed Oct. 6, 2003, the disclosures of which are incorporated by reference.

BACKGROUND OF THE INVENTION

1. Field of the Invention

A method and an apparatus for finding the location of one or more holes in a fluid flow system such as a pipe, duct, or conduit, using one or more tracers that interact with or can be chemically or physically differentiated from the liquid or gas contents located outside the system and pulled back into the system when the system is placed under a vacuum. The invention is particularly applicable to underground pipes. This invention is related to the invention disclosed in U.S. patent application Ser. No. 10/960,653, filed Oct. 6, 2004, titled Method and Apparatus for Detecting and Locating Explosives, Biological, and Chemical Substances in Ducts and Structures Using Tracers.

2. Brief Description of the Prior Art

Locating holes in piping, especially underground or buried piping is a challenging and important problem. It has both environmental and economical implications. A method for accurately locating a leak in underground pressurized piping is of immediate benefit to the petroleum, chemical, and nuclear industries.

This specification describes a method and an apparatus for finding the location of one or more holes in a fluid flow system such as a pipe, duct, or conduit, using one or tracers that are injected into the system and that interact with or can be differentiated chemically or physically from the liquid or gas contents outside the system when pulled back into the system under a vacuum. PCUT is an acronym for Pipeline Characterization Using Tracers, and characterization includes detection, location, and quantification of a contaminant in the pipe. The PCUT technology was demonstrated in a pipe using a thin layer of diesel fuel trapped at the bottom of the low point of the pipe as the contaminant. The method of the present invention differs from the method for detecting and locating contamination in a pipe, because the contamination was already present in the pipe. In the present invention, a vacuum is generated in the pipe to pull in the released liquid (or gas) contents of the pipe that was released or leaked through a hole in the pipe wall. Once the released contents are pulled back into the pipe, the PCUT technology applies, using the released contents that were pulled back into the pipe as a marker of the location of the leak hole.

There are a number of methods used to locate a hole in a pipe. These methods have been used to find holes in pipelines containing petroleum fuel, natural gas, dangerous chemicals, and radioactive liquids. The most conventional approach is to insert a tracer into the pipe and search for it outside the pipe. If the tracer is detected, and if it is unique (i.e., not part of the background environment), the presence of the tracer outside the pipe is an indication that the pipe has a hole. The location of the tracer is an indication of the location of the hole. For example, helium is often used as a tracer.

When the pipe is buried underground, which is the most common need for the method of the present invention, a carefully designed sampling procedure is required to detect the presence of the tracer. While liquid tracers can be used, gaseous tracers or liquid tracers that volatize when released into the ground are the most often used, because gaseous tracers rise to the ground surface where their presence can be detected. Closely spaced vapor samples along the length of the pipe with a hole are required. Liquid tracers are not as common or cost effective for this application, because once the tracer is released into the soil, it is not easily sampled. The use of gaseous tracers is expensive to implement and has many technical pitfalls. It is expensive to implement, because samples must be collected at 5- to 20-ft intervals to avoid missing the presence of the tracer, and the tracer material is generally expensive. Technically, the location of the underground pipe must be well known for the method to work. If the samples are too far off the centerline of the pipe, the presence of any tracer can be missed. A larger problem is that the subsurface soil is not homogenous and the tracer will tend to follow underground pathways and rise to the surface off the centerline of the pipe. Finally, the performance of the method depends on the nature of the tracer. For best performance, the tracer must be unique and not be present in the environment. In some cases, constituents in the pipe fluid are used. These have not been very effective because previous releases and spills of the pipe contents contaminate the soil. Adding a tracer to the pipe that is unique and is not present in the pipe fluid or the surrounding soil is the most effective. However, both types of tracers have resulted in false alarms because of their presence in the surrounding soil. While there are technical pitfalls, this technique has been widely applied.

Another approach is to use passive acoustics. Two acoustic sensors are attached to the pipe in such a way that the sensors bracket the hole. The pipe is then pressured so that an acoustic signal is generated at the hole. This technique will work with both liquid- and gas-filled pipes. However, the acoustic leak signal generated in a gas-filled pipe is much weaker than the acoustic signal generated in a liquid-filled pipe. Advanced signal processing using correlation and coherence analysis algorithms are required for accurate location estimates. The distance between the sensors on the pipe, and a good estimate of the acoustic propagation velocity are required to make accurate location estimates. In general, for small holes, sensor separations must not be too much greater than 100 ft for gas-filled pipe and 500 ft for liquid-filled pipe. Also, access to the pipe is required to mount the sensors on the pipe. This can be expensive if the pipeline to be interrogated is long and the pipe has to be excavated at many locations to obtain the required spacing to implement the method. This technique is also widely used, but is best used in pipe applications where the pipe is on the order of 500 to 1,000 ft or where access to the pipe exists (e.g., at valve pits).

There are other approaches to locating a hole in a buried pipe. There are infrared sensing methods that detect the presence of the released pipe contents from a change in temperature between the contaminated and uncontaminated regions. This approach has not been very effective.

There are other approaches to locating a hole in a buried pipe. There are infrared sensing methods that detect the present of the release pipe contents from a change in temperature between the contaminated and uncontaminated regions. This approach has not been very effective.

There is a need for a method that does not require sampling at closely spaced intervals at the surface or excavation to the top of the pipe for implementation of the method. There is a need for a method with higher performance than the tracer, acoustic and infrared systems now in use. Stated differently, there is a need for a method that can be used on long sections of pipe that is both more reliable and more accurate than these three methods. Finally, there is a need for a method that is less expensive than these current methods.

The method of the present invention uses a gaseous tracer method developed by the inventors to locate a hole in a pipe. While the invention can also detect the presence of a hole, there are more reliable, accurate, less expensive methods, and commercially available methods, such as volumetric and pressure-based methods, that are used that can perform this task. These detection methods outperform and are less expensive than the tracer, acoustic, and infrared methods mention above. The method is called PCUT (Pipeline Characterization Using Tracers). A gaseous tracer that interacts with the contaminant of interest is used. Both partitioning and reactive tracers can be used for this application. The method described here is very similar to the one described in two patent applications submitted by the inventors for characterizing (detection, location, and quantification) contamination in pipes, ducts, and other fluid flow systems, and for find dangerous and hazardous substances like explosive devices in ducts, buildings and the like. However, the application objective is very different, but the technology for location, which is required for this application, is very similar.

Figure 1:
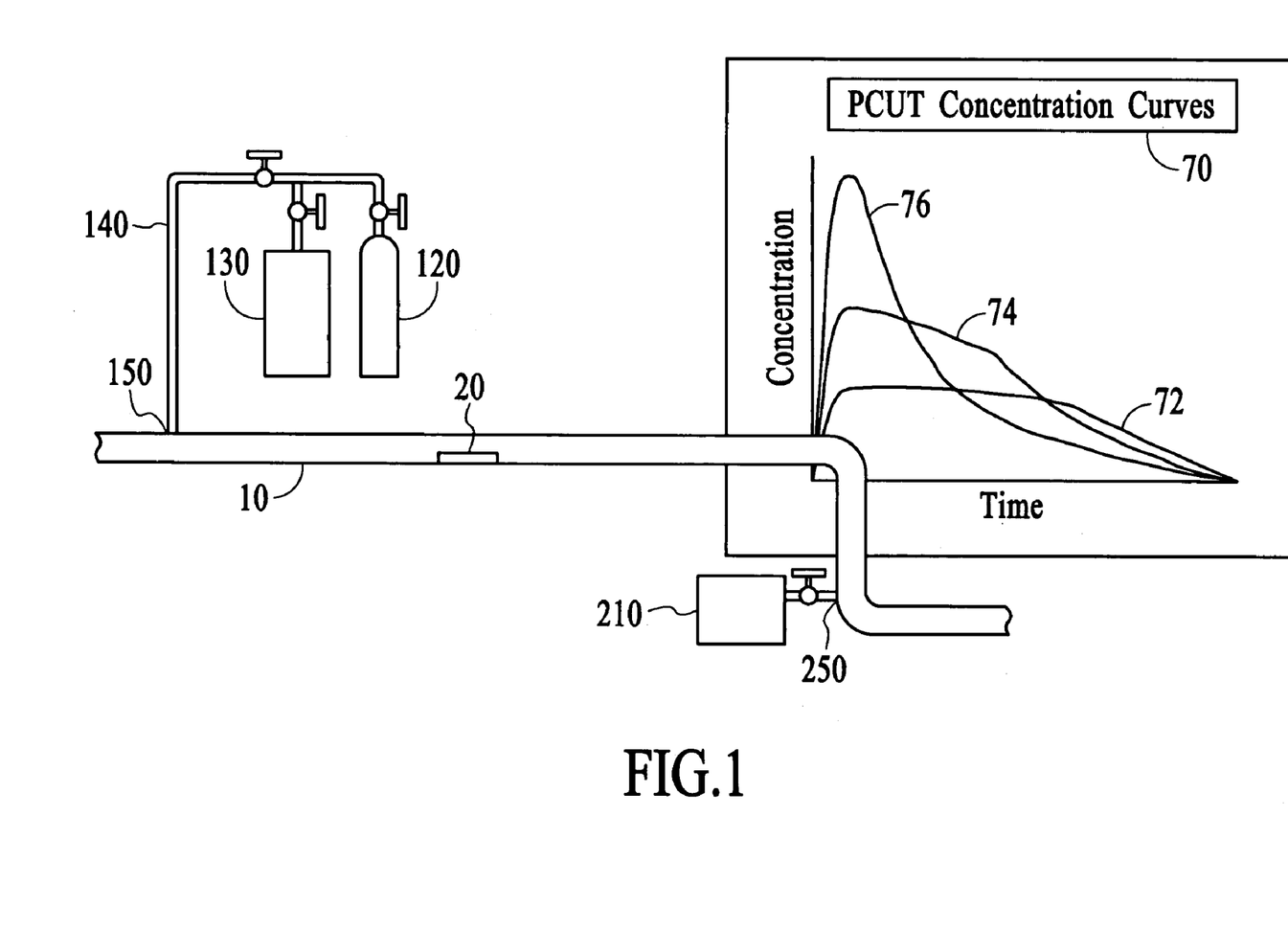
FIG. 1 is a simplified illustration of the method for characterizing contamination in pipes and ducts. The time history of the elution curves of tracer concentration for both the conservative and the partitioning tracers are shown.

FIG. 1 is a simplified illustration of the use of PCUT for detecting and locating the presence of a liquid contaminant, such as diesel fuel, in a pipe, using a conservative tracer and two partitioning tracers. As illustrated in FIG. 1, the method was implemented by injecting a "slug" of two tracers 120 and 130 into a pipe 10 or other fluid flow system, with different partitioning coefficients ($K_i$). One of the tracers is a conservative tracer, i.e., it will not dissolve, adhere, or interact with the hazardous substance of interest. The other tracers are selected so they will dissolve, adhere or interact with the hazardous substance of interest. The tracers are transported or advected from the injection point 150 (at one location in the pipe) to one or more extraction points 250 (at other locations in the pipe) by a gas flow field established in the pipe prior to the injection of the tracers 120 and 130. The gas flow field used to transport the tracers is typically nitrogen or air, because they do not generally interact with the tracers or the hazardous substances in the fluid flow system. The velocity of the advection flow field is selected so that the tracers have enough time to fully dissolve, adhere or interact with the hazardous substance before the leading edge of the tracer reaches the extraction point and is measured with a gas chomatograph (GC) or some other sensing means that can measure the magnitude of the tracers reaching the measurement point 250. At that point, no more tracer is introduced into the line. By measuring the time history of the concentration 70 of the partitioning 72, 74 and the conservative 76 tracers at the extraction point in the pipe, the presence and amount of the contaminant within the pipe or duct can be determined.

Detection and quantification can be accomplished using the difference in the mean arrival time of the partitioning and conservative tracers, or the difference in the levels of concentration between the conservative and partitioning tracers. The location of the contaminant can be determined by introducing a perturbation to the advection flow field. This can be accomplished by flushing (i.e., removing) the conservative and partitioning tracers in the line, and then measuring the mean time of arrival of the partitioning tracers that are still being eluted from the contamination in the system. Alternatively, this can be accomplished by introducing enough partitioning tracer at the beginning of the duct test to cover the entire duct, then stop the flow, and allow the tracer to interact with dangerous or hazardous substance. After a period of time, an advection flow field is established, and GC samples are collected and analyzed.

A series of over 25 laboratory experiments were conducted to demonstrate the capability of PCUT for detecting, locating, and quantifying a contaminant using one or more interactive tracers, and for some measurements, one or more conservative tracers. The location capability of the PCUT technology was demonstrated in the laboratory using the 116-ft, long-pipe illustrated in FIG. 12. The long pipeline 900 (116 ft) is comprised of 66-ft of 2-in.-diameter pipe 910 between the inlet 902 and the first 4-ft 3-in.-diameter section of PVC pipe 912 and 45-ft of 2-in. PVC pipe 914, 916, 918 between the first 3-in.-diameter PVC pipe section 912 and the outlet 904. The second 3-in.-diameter PVC pipe section, which could be used as a contamination point, was not used in the location tests presented herein.

Figure 12:
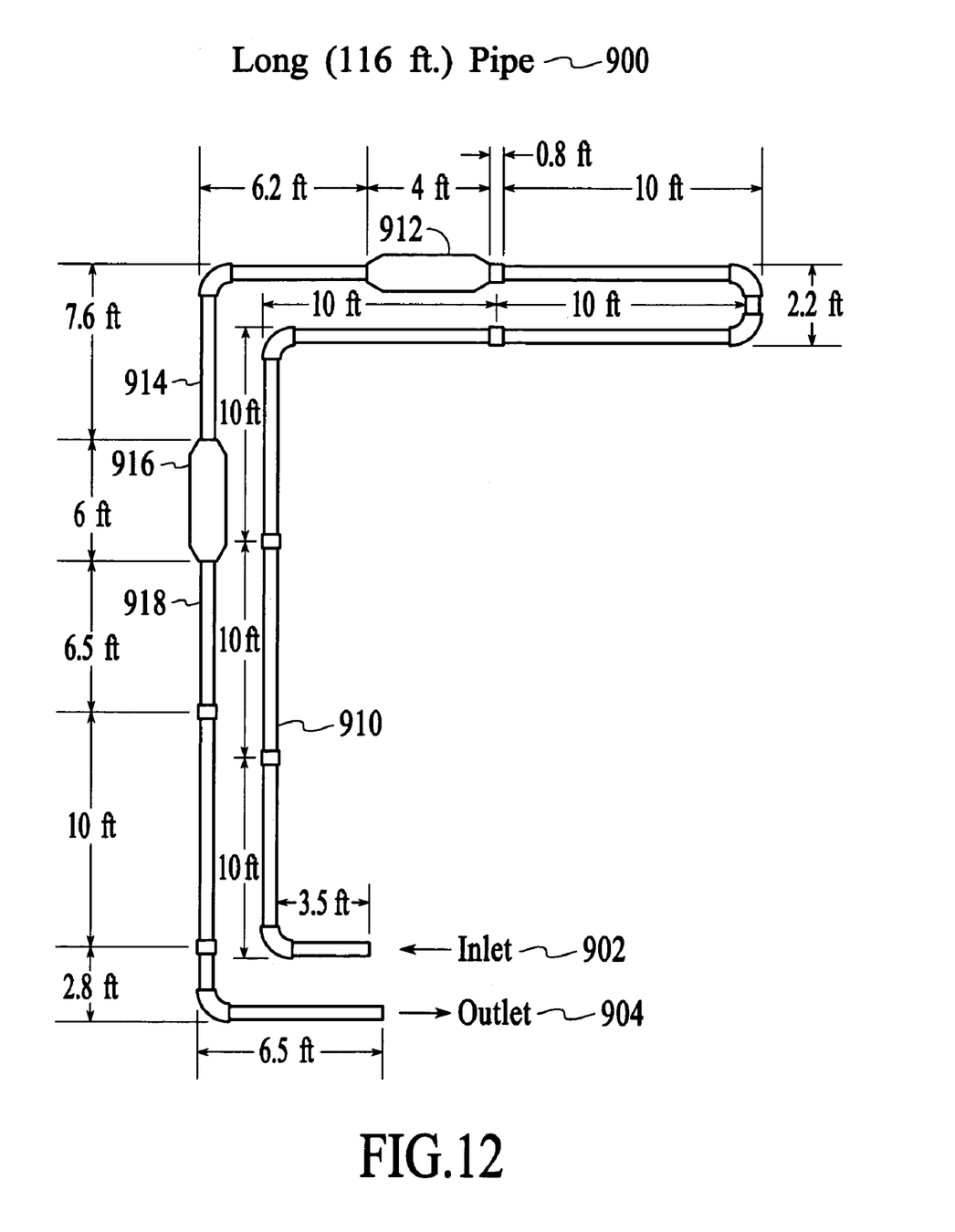
FIG. 12 illustrates a schematic of a pipeline used in laboratory testing.

A 3-ft by 1.625-in. rectangular tray was inserted into the 4-ft section of 3-in. diameter PVC pipe 912 whose center position was located 47.5 ft from the outlet end of the pipe 904 where the GC measurements were made. The shallow tray was used to hold 300 ml of aged diesel fuel. Two partitioning tracers ($C_7F_{14}$ and $C_8F_{16}$) were used for these tests. The advection gas was nitrogen.

Figure 13A:
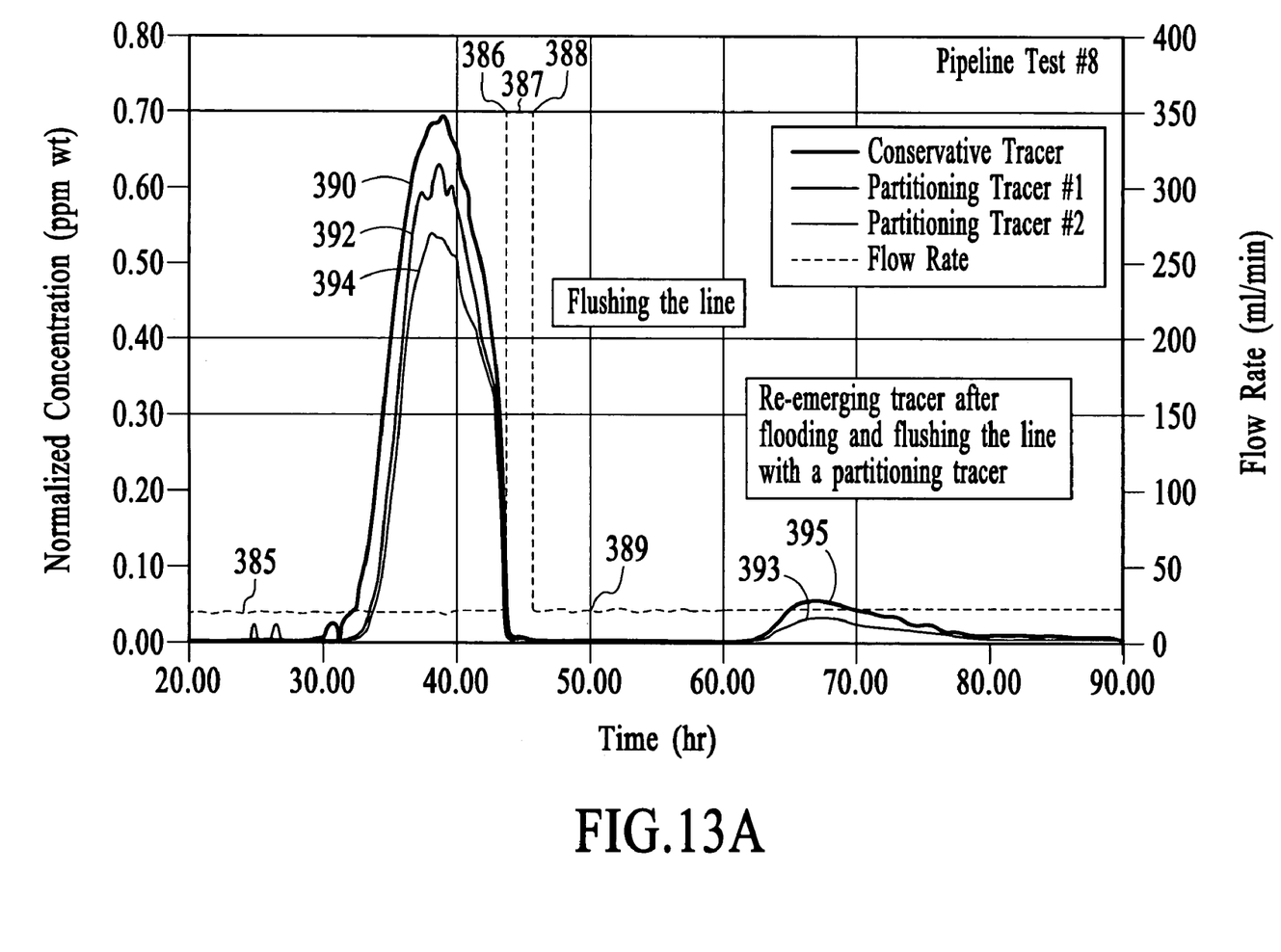
FIG. 13a illustrates test results from a test to determine the location of contamination within the long pipe using 300 ml of diesel as the contaminant located at two thirds of the pipe length.
Figure 13B:
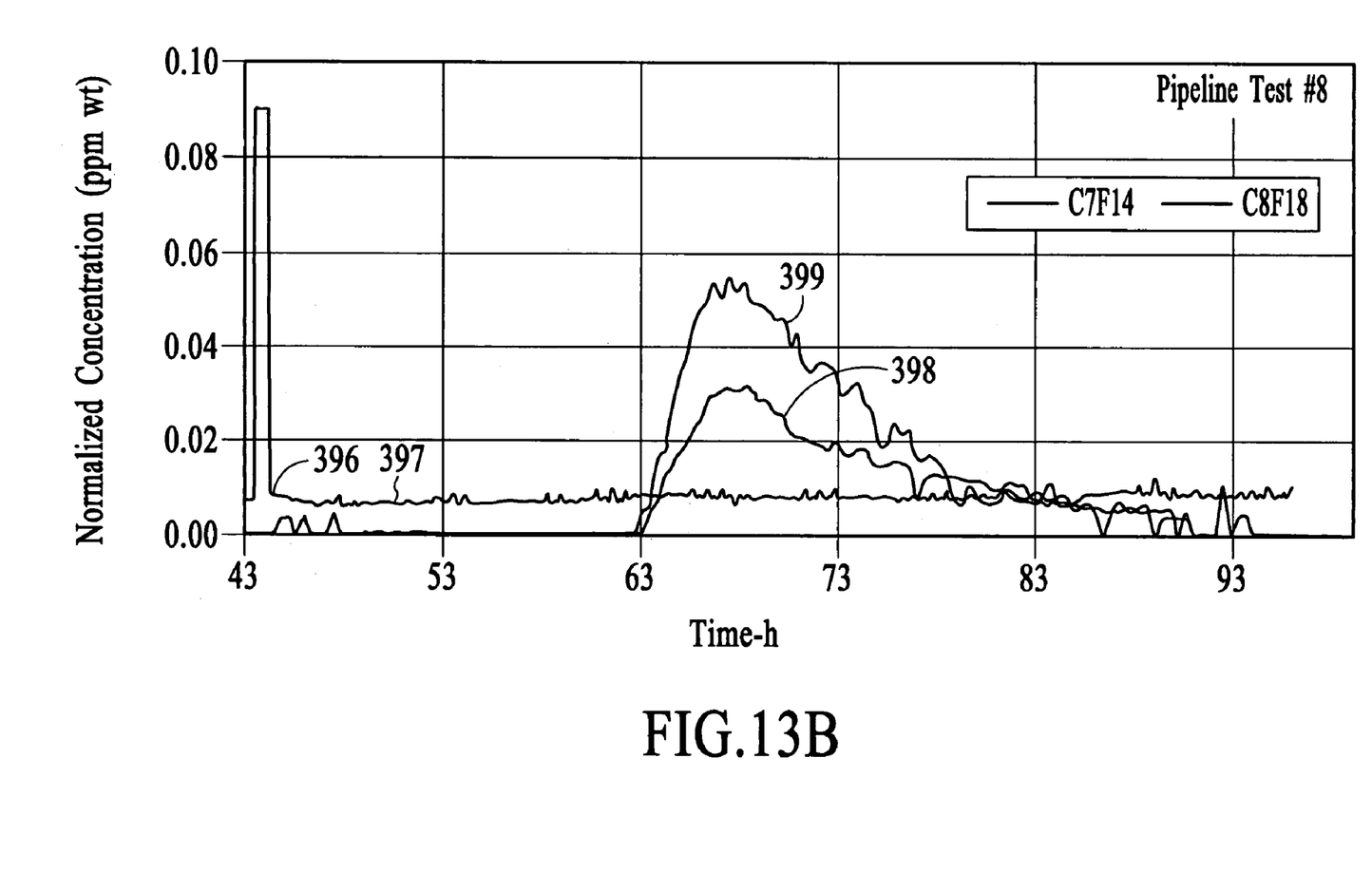
FIG. 13b illustrates a tracer concentration curve that re-emerges from the contaminant after the line has been flooded and flushed.

FIG. 13a shows the time history of the concentration curves of the two partitioning tracers 392, 394 and the conservative tracer 390 from one of the location tests (Pipe Test #8). Superimposed on these curves is the flow rate of the advection gas 385, 387, 389. The location measurement is made after the detection measurement. The data required for detection is the same as for previous tests except only enough data needs to be collected to define the peak of the conservative tracer. This allows a comparison between the partitioning tracers and the conservative tracer for detection and also allows sufficient time for the tracers to partition into the contaminant. The next step is to rapidly flush 387 the conservative and partitioning tracers through the pipe and then to re-establish the advection flow stream 388 at a known velocity 389. As shown in FIG. 13a, the line was flushed at 350 ml/min 387, which is over 10 times the initial flow rate of the measurements 385. Once the flow rate is re-established 388 at a flow rate of approximately 20 ml.min 389, the partitioning tracers 393, 395 in the diesel fuel re-enter the flow stream and are advected to the end of the line at a known flow rate 389. The location of the contamination was then determined from the advection velocity 389 and the arrival time of the tracers. The arrival time is the time between the end of the flush 388 at the high flow rate 387 and the arrival of the partitioning tracers 393, 396 being emitted from the contamination. FIG. 13b shows the two partitioning tracers 398, 399 arriving at about 63 hours; the advection flow field 397 was re-established at 44 hours 396.

Table 1 summarizes the location results for the tests conducted in the long pipe 900 illustrated in FIG. 12. Two methods were used to locate the contamination. Both methods used the time of arrival of the leading edge of the tracer concentration curves. (The average time of arrival can also be used.)

TABLE 1

PCUT estimation of the location of the 300 ml of diesel fuel contamination.

| Test | Method 1 | | Method 2 | |
| --- | --- | --- | --- | --- |
| | Location (ft) | Error (%) | Location (ft) | Error (%) |
| Pipe Test #8 | 51.3 | 3.3% | 53.2 | 4.9 |
| Pipe Test #10 | 38.1 | 6.4% | | |
| Pipe Test #12 | 45.4 | 0.1% | | |
| Pipe Test #23 | 44.7 | 0.6% | | |
| Average | | 2.6% | | |

* The actual location of the contamination is centered 47.5 ft from the outlet end of the 116-ft pipe.

The first method, which requires a priori information about the diameter or geometry of the pipe, uses the maximum velocity of the advection fluid within the pipe and the time of arrival of the tracer(s) after flushing. The average velocity is computed by dividing the measured volumetric flow rate by the diameter of the pipe; the maximum velocity (for laminar flow in a pipe) is twice this value. The second method, which does not require a priori information about the diameter or geometry of the pipe, only the total length of the pipe, utilizes the ratio of the time of arrival of the leading edge of the first tracer pulse 392 or 394, which traveled over the full length of the pipe (i.e., 116 ft) 900 and the time of arrival of the second tracer pulse 393 or 395, which traveled only the distance from the contamination 912 to the outlet end 904 of the pipe 900. After weighting the arrival times by the mean of the measured flow rates, the distance from the outlet end 904 of the pipe to the contamination 912 can be determined. Both methods were applied to Pipe Test #8 and only the first method was applied to Pipe Tests # 10, #12, and #23.

The location test was also repeated (Pipe Test #12) using a dried glue sample of approximately 20 grams (10 ml). For this test the pipeline was flooded with tracer overnight and then flushed with 350 ml/min of the advection gas. After the flush, an advective flow stream was established and used to determine the location of the dried glue specimen. The distance from the end of the pipe to the glue sample was calculated to be 49.2 ft which is less than 10% error on the actual value of 47.5 ft.

SUMMARY OF THE INVENTION

It is the object of this invention to provide a method and an apparatus for locating holes in pipes, ducts, conduit, or other type of fluid flow systems without having to physically, robotically, or mechanically enter the system. The method and apparatus can be used for both underground and aboveground fluid flow systems.

Another object of this invention is to provide a method and an apparatus for locating holes in underground pipes, ducts, conduit, or other type of fluid flow systems.

It is also an object of this invention to provide a method and an apparatus for locating holes in long pipes, ducts, conduit, or other type of fluid flow systems.

It is another object of this invention to provide a method and an apparatus for locating holes in pipes, ducts, conduit, or other type of fluid flow systems without having to collect samples on the ground above the pipe.

Still another object of this invention is to provide a method and an apparatus for locating holes in pipes, ducts, conduit, or other type of fluid flow systems without having to excavate pits along the pipe to attach sensors to the pipe.

It is a further object of this invention to provide a method and an apparatus for locating holes in pipes, ducts, conduit, or other type of fluid flow systems with access to the pipe at only two locations.

Another object of this invention is to provide a method and an apparatus for detecting holes in pipes, ducts, conduit, or other type of fluid flow systems without having to physically, robotically, or mechanically enter the system.

For the purposes of this specification, the method and its alternative embodiments will be described first in terms of locating a hole in an underground pipe containing petroleum fuels (e.g., diesel fuel), a very real problem. This application will be particularly illustrative, because the PCUT technology for detecting, locating, and quantifying contamination in a pipe was demonstrated using diesel fuel as the contaminant. However, it must be understood that the method and apparatus are not limited to this application and will work equally well for other liquids or gases and other pipe configurations. For example, the method can also be used for locating holes in aboveground pipes and pipes in buildings and other structures. In addition, the method can be used for pipes containing both liquids and gases provided that all liquids are removed from the pipe before the method is applied. Also, while the method is described first in terms of pulling back into the pipe the contents that were released through the hole in the pipe due to the leak (e.g., diesel fuel), gases and liquids in the ambient environment or gases in the ambient environment surrounding the pipe, either resident or placed there for the leak-location measurement, can also be used. The method will be described in terms of locating only a single hole in the pipe, but the method can be used to find multiple holes. Finally, the method will be described in terms of one tracer, but multiple tracers can also be used. Applications for ducts and conduits follow directly for someone skilled in the art.

Figure 2:
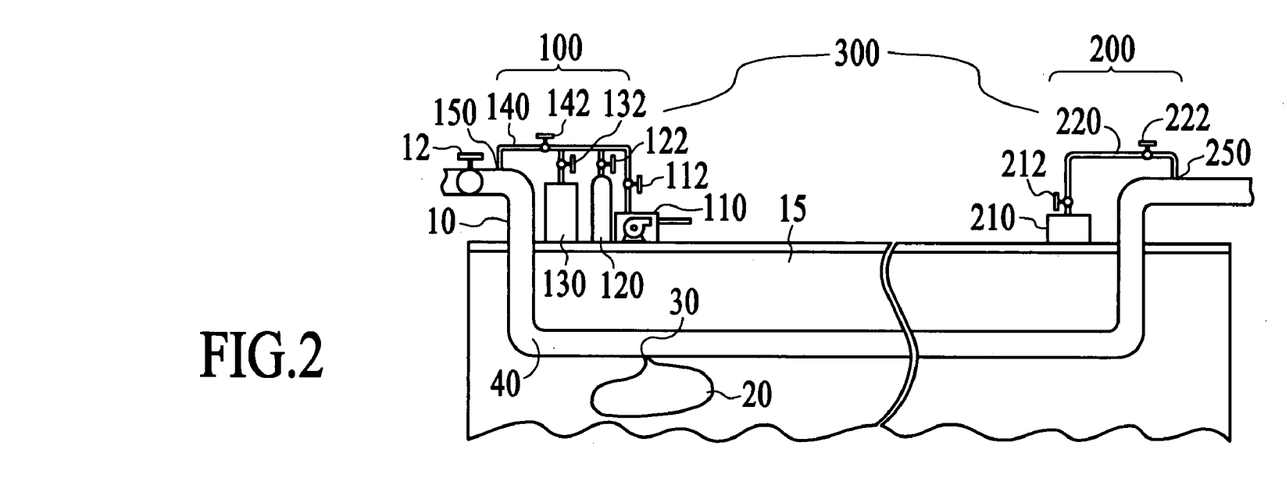
FIG. 2 is a simplified illustration of the method of the present invention for locating a hole in an underground pipe after a release or leak has occurred, the liquid in the pipe has been removed, and the inside of the pipe has been cleaned.

FIG. 2 shows a simplified illustration of the present invention 300 for location of a hole 30 in an underground pipe 10 that has released the liquid contents of the pipe 10, such as diesel fuel, into the ground 15 around the pipe 10. The plume 20 of the released contents in the vicinity of the hole 30 in the pipe 10 is also shown in FIG. 2. The tracer injection system 100 with a vacuum pump 110 is shown on one end of the pipe, and the tracer measurement system 200 is shown at another location of the pipe downstream of the leak hole 30. The tracer measurement system 300 is identical to the one used for the application of PCUT for finding contamination in a pipe except for the vacuum pump 110. The tracer injection system 100, which attaches to the pipe 10 at 150, is comprised of a tracer injection container 130 and a valve 132, a pressured bottle of inert gas 120 and a valve 122, a vacuum pump 110 and a valve 112, and a valve 142 on the communication conduit 140 to isolate the pipe 10 from the tracer injection system 100. The tracer measurement system 200, which attaches to the pipe 10 at 250, is comprised of a gas chromatograph (GC) 210, or some other analytical measurement system, and a valve 212, a valve 222 on the communication conduit 220 to isolate the pipe 10 from the tracer injection system 200.

The preferred method of hole-location using the present invention is applied to an empty pipe or section of pipe that can be isolated with valves or blinds. If the pipe contains a liquid, then it must be emptied and cleaned before the method can be applied. The overall approach is to draw a vacuum on the pipe so that any of the released fluid from the pipe will be brought back into the pipe at the location of the hole so that it can interact with the tracer or tracers used for detection and location. The first step is to flood the pipe with a gaseous partitioning tracer selected to interact with the released pipe contents (i.e., the contaminant). The second step is to draw a vacuum over an established time period to pull back into the pipe any of the liquid or gas released from the pipe, which may reside in the surrounding soil in the immediate vicinity of the hole. Once the contaminant is back in the pipe, the third step is to allow sufficient time is allowed for the tracer to interact with the contaminant. The fourth step is to establish a known advection flow in the pipe by introducing a gas that does not interact with the contaminant or tracer at the inlet side of the pipe. The advection flow is slow enough to transport the fluid in the pipe without significant mixing. The fifth step is to extract the gas in the pipe at the outlet side of the pipe and to measure the concentration of the tracer as a function of time with a gas chromatograph or another analytical instrument. The location of the hole is determined from the time of arrival of the lower concentration tracer gas that interacted with the contaminant and the velocity of the advection flow field.

This method can be more robust if a partitioning tracer is used. If a partitioning tracer is used, all of the gas in the pipe can be flushed from the line after allowing the tracer to partition into the contaminant and before establishing an advection field. In this case, only the presence and time of arrival of the partitioning tracer that has been emitted from the hole-contaminant need be detected. This is more robust because edge mixing with the tracer in the first implementation is avoided.

DETAILED DESCRIPTION OF THE PREFERRED EMBODIMENT

Figure 3:
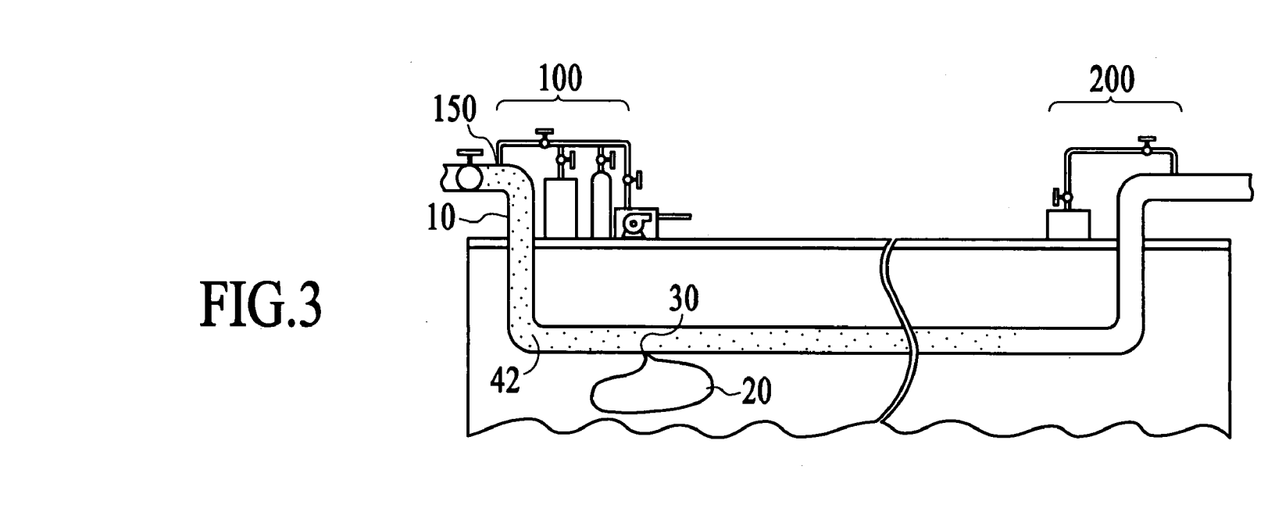
FIG. 3 is a simplified illustration of the method of the present invention for locating a hole in an underground pipe that has leaked and after the pipe has been inundated with one or more partitioning tracers.
Figure 4:
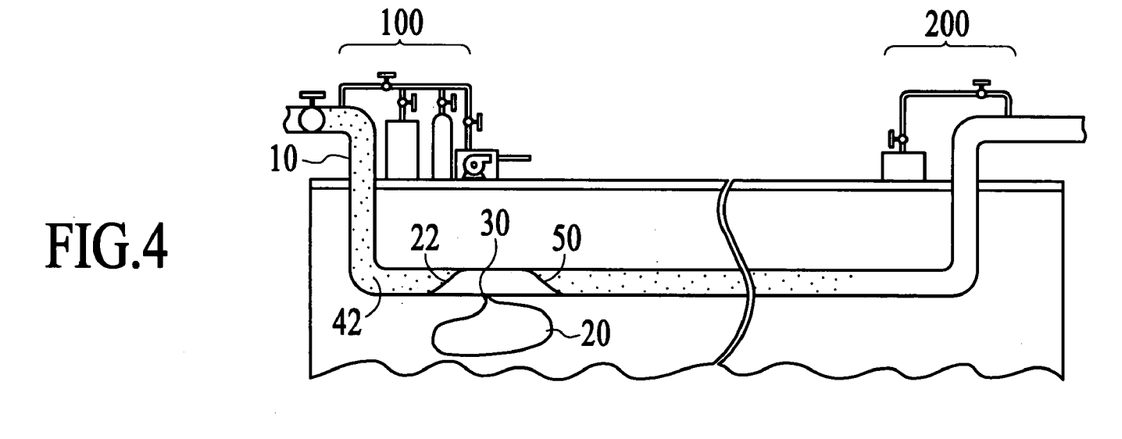
FIG. 4 is a simplified illustration of the method of the present invention for locating a hole in an underground pipe that has leaked and after the pipe has been inundated with one or more partitioning tracers, and a vacuum has been pulled on the pipe. The released material pulled back into the pipe and the interaction of the tracer with this material are shown.

The preferred embodiment of the method and apparatus shown in FIG. 2 requires the interaction of one or more gaseous tracers 130 injected into a pipe 10 (see FIG. 3) and the liquid or gas contents pulled back into pipe from the plume 20 at the location of a hole 30 when the pipe is placed under a vacuum (see FIG. 4). The location of the hole 30 will be marked by the material pulled back into the pipe from the contamination plume 20 created by the leak. The preferred embodiment of the present invention illustrated in FIG. 2 further requires that the line be empty 40 before the start of the location measurement. This may require pumping out all of the liquid or gas from the pipe. In the case of a diesel fuel pipeline, the diesel fuel can be pumped back into the underground or aboveground storage tank used to supply fuel to the pipe. If the tracer used is designed to interact with the pipe contents and the slug of material pulled back into the pipe is the same as the contents that were released, it might be necessary to flush the pipe with an inert gas, water, or some other cleaning solvent before injecting the tracer into the pipe. The pipe should be cleaned sufficiently so that the original contents of the pipe will not interact with the tracer. This may not be true if water or air is pulled back into the pipe and this is the quantity to detect.

Figure 5:
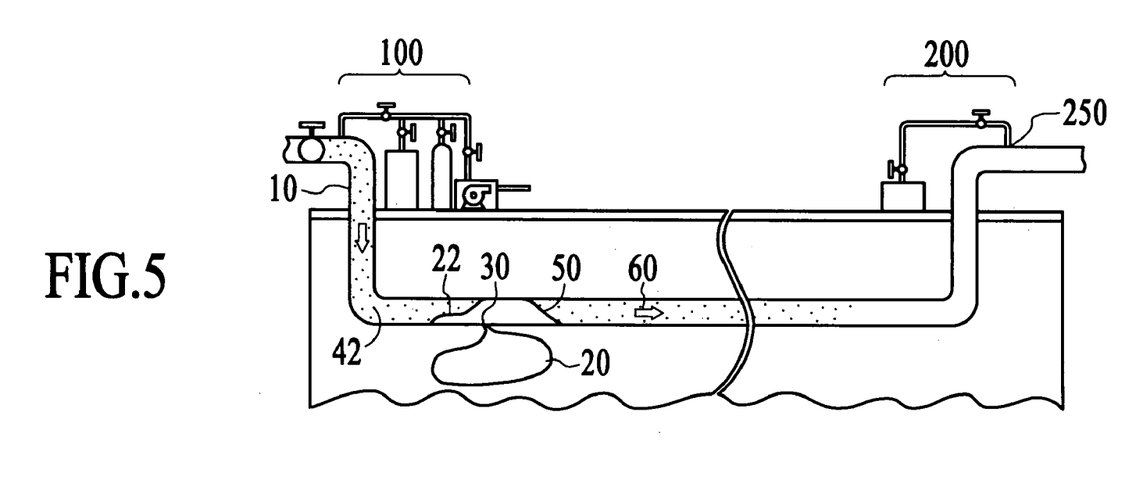
FIG. 5 is a simplified illustration of the method of the present invention illustrated in FIG. 4 after the tracers in the pipe are being advected with an inert gas toward the tracer measurement point.

As illustrated in FIG. 3, a tracer 42, which will interact with the liquid or gas contents located outside 20 and in the immediate vicinity of the hole 30 in the pipe 10, is injected into the pipe 10 being tested in such a way that the entire line is filled with the tracer 42. Then, the pipe is placed under a vacuum, as illustrated in FIG. 4, so that a slug of liquid (or gas) material 20 located in the plume outside the hole 30 in the pipe is pulled back into the pipe through the hole 30 in the pipe 10. This slug of liquid material 22 pulled back into the pipe interacts with the tracer in the pipe in such a way that it changes the physical or chemical properties of the tracer 50 in the immediate vicinity of the hole in the pipe. In general, this interaction results in a lower concentration of the interactive tracers. As illustrated in FIG. 5, the entire contents of the pipe are then advected to a monitoring point 250 located downstream of the hole in the pipe using an inert gas, such as nitrogen or air, that does not interact with the material 22 pulled back into the pipe 10. Both reactive and partitioning tracers can be used. The advection velocity 60 is selected so that the tracer in the immediate vicinity of the hole will be mix back into the surrounding tracer gases such that it is undetectable at the downstream measurement point. If a location estimate is desired, then the advection velocity should be at a known flow velocity. Careful control of the flow velocity is not required if only detection is desired.

Figure 6:
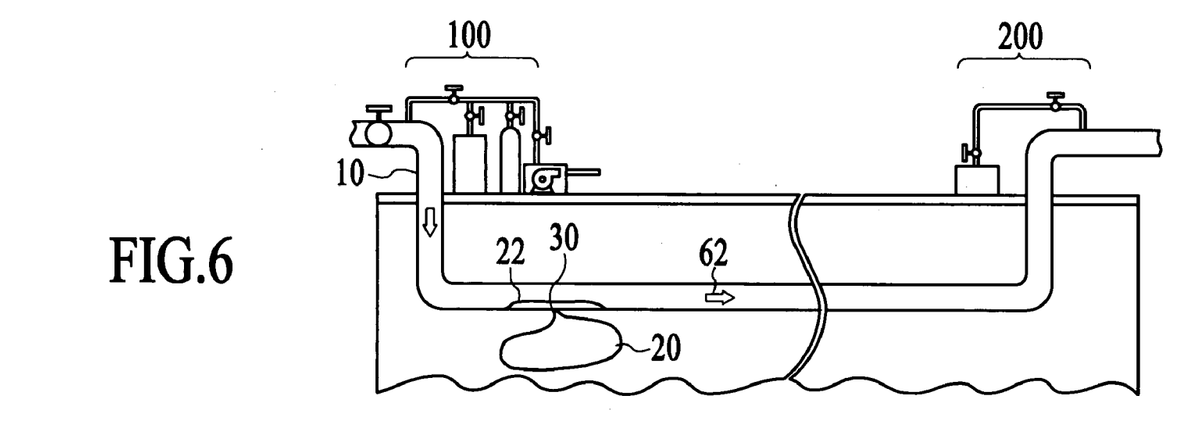
FIG. 6 is a simplified illustration of the method of the present invention for locating a hole in an underground pipe shown in FIG. 4 after the tracer in the pipe and the slug of tracer that has interacted with the released material pulled back into the pipe have been removed from the pipe by rapidly flushing these tracers gases through the pipe with an inert gas.
Figure 7:
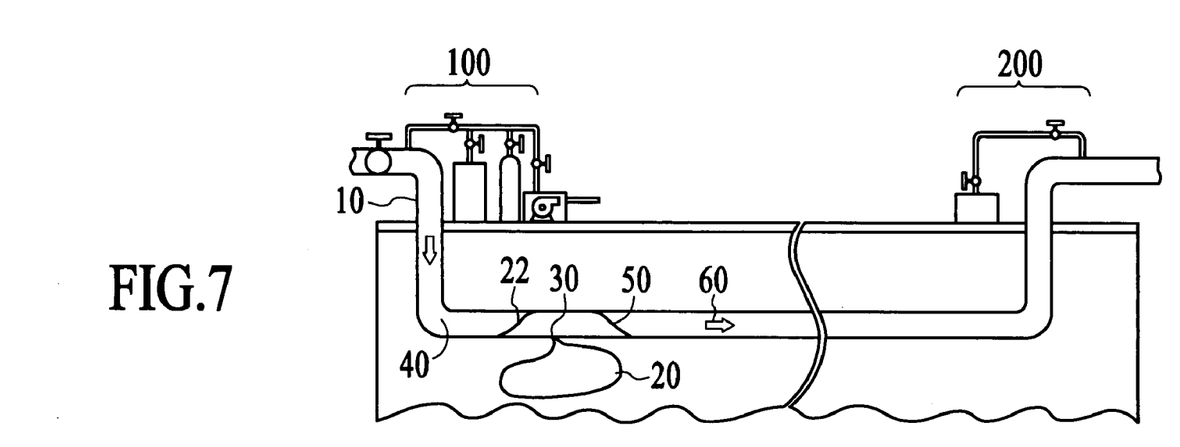
FIG. 7 is a simplified illustration of the method of the present invention for locating a hole in an underground pipe after the tracer material has been flushed from the pipe, as shown in FIG. 6, and the partitioned tracer in the released material pulled back the pipe has begun eluting tracer back into an advection flow stream whose velocity is known.

Alternatively, if partitioning tracers are used, then the tracer gas or gases in the pipe shown in FIG. 4 can be quickly flushed at a high advection velocity 62, as illustrated in FIG. 6, using the advection gas (e.g., nitrogen). Once the pipe is free of tracers, then the only tracer that will be in the pipe is the tracer that partitions from the material 22 that was brought back into the pipe from the external plume 20 of the released pipe contents. As illustrated in FIG. 7, this tracer eluting 50 from the material 22 is then advected down the pipe at a controlled flow velocity.

The location of the hole in the pipe is determined from the time of arrival of the tracer or tracers that interacted with the slug of material 22 pulled back into the pipe 10 through the hole 30 in the pipe 10. Using the known geometry of the pipe and the known advection velocity, the location in terms of distance can be determined.

The tracer measurement can also be accomplished at the same location that the tracers were introduced when an inert advection gas is not used to advect the tracers down the line to the measurement point; this would require, however, that a vacuum be pulled on the line to transport the tracers back to the injection point.

The selection of the tracer and the duration of the test depends on whether or not (1) a liquid or gaseous contaminant is pulled back into the pipe that interacts chemically with the tracer and changes the concentration of the tracer in the immediate vicinity of the hole, or (2) air, water, or the released pipe contents that do not interact with the tracer is pulled back into the pipe and displaces a volume of the gaseous tracer with a non-interactive substance or liquid contents of the pipe with an immiscible liquid (e.g., fuel and water). In both cases, the concentration of the tracer in the immediate vicinity of the hole is lowered. The advection velocity must be selected so that this slug of lower concentration tracer moves along the pipe to the measurement point downstream of the hole without getting mixed back into the tracer located on either side of the slug. A gas chromatograph 210, located at the measurement point 250, is used to monitor the concentration of the transported tracer. As stated above, the location of the hole can be determined from the time of arrival of the tracer with lower concentration, and the distance from the inlet or outlet can be determined from the time of arrival and the transport velocity.

As illustrated in FIGS. 1 and 2, the apparatus needed to apply the leak-location method is the same one used for finding contamination in a pipe. A GC is required if the concentration of the tracer needs to be measured at the downstream monitoring point. If the material pulled back into the pipe is inert such as air or water, which is distinguished from the tracer placed into the pipe, because it displaces a large enough volume of tracer to be detected, then a simpler detection measurement system than a GC that samples for water or air can be used. A simpler device can also be used if it has the capability of sensing the presence of the tracer or tracers used in the test.

DESCRIPTION OF ALTERNATIVE EMBODIMENTS

First Alternative Embodiment

The above method, in which the entire line is initially flooded with a tracer, can be used to regardless of what type of material, liquid or gas, is ingested back into the pipe at the location of the hole. Alternatively, if the liquid contents released from the line are pulled back into the line when the vacuum is placed on the line, then only a slug of tracer gases are required for detection and location. Once the released liquid is pulled back into the line, the PCUT method and apparatus is then used to locate the leak hole using the contamination as an indicator of the hole location.

Figure 8:
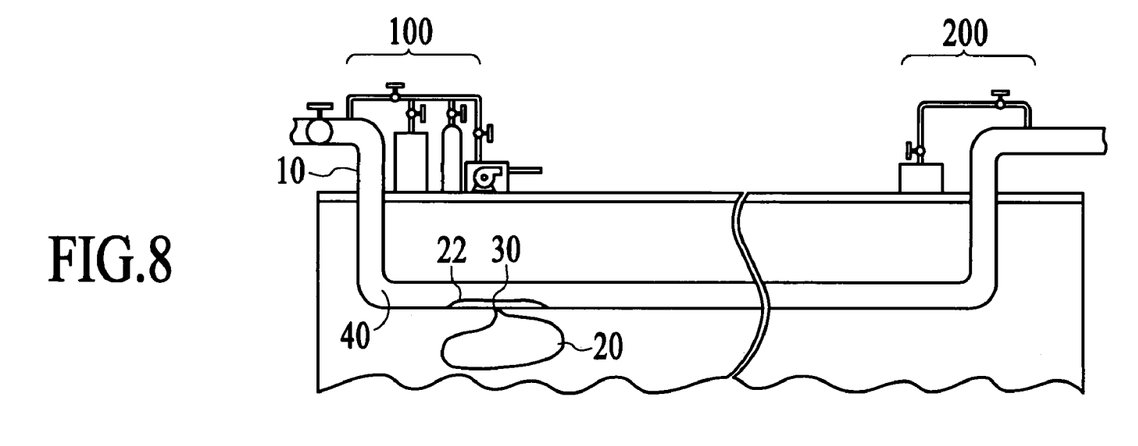
FIG. 8 is a simplified illustration of the method of the present invention for locating a hole in an underground pipe that has leaked and after a vacuum has been pulled on the pipe. The released material pulled back into the pipe is shown.

In this alternative embodiment, the pipe shown in FIG. 2 is first cleaned by flushing with an inert gas or water or some other cleaning substance. The pipe should be cleaned sufficiently so that the original contents of the pipe will not interact with the tracer. Then, as illustrated in FIG. 8, a vacuum is pulled on the pipe and any liquid in the plume 20 in the vicinity of the hole 30 is pulled back into the pipe 10. A tracer is then selected that will partition into the released contaminant when such contamination is pulled back into the pipe at the location of the hole. In contrast to the preferred embodiment, the vacuum is pulled on the pipe before the tracer is injected into the line and only a slug of tracer is used. The entire fluid volume of the pipe does not need to be inundated with tracer.

Figure 9:
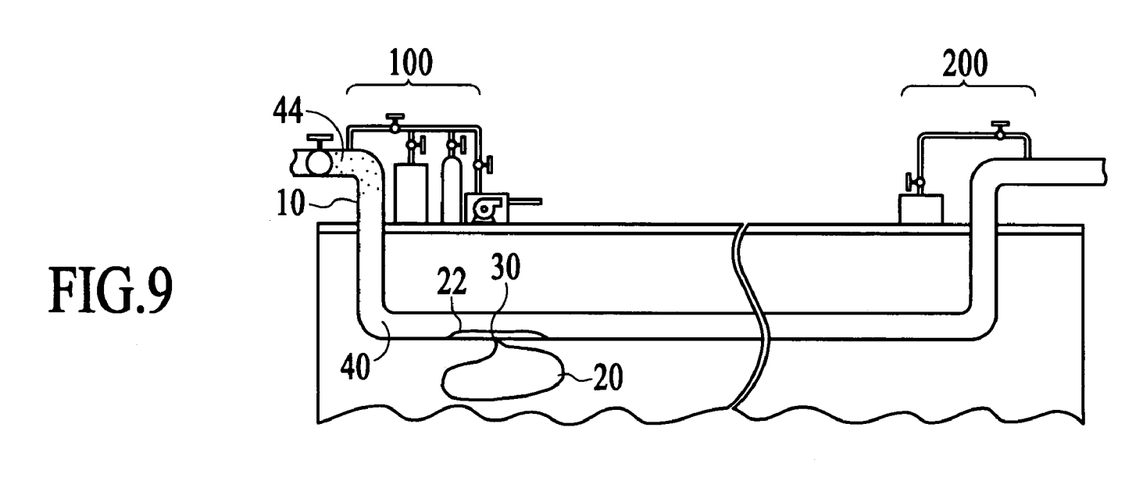
FIG. 9 is a simplified illustration of the method of the present invention for locating a hole in an underground pipe that has leaked and after a vacuum has been pulled on the pipe, and a "slug" of one or more partitioning tracers have been introduced into the pipe.
Figure 10:
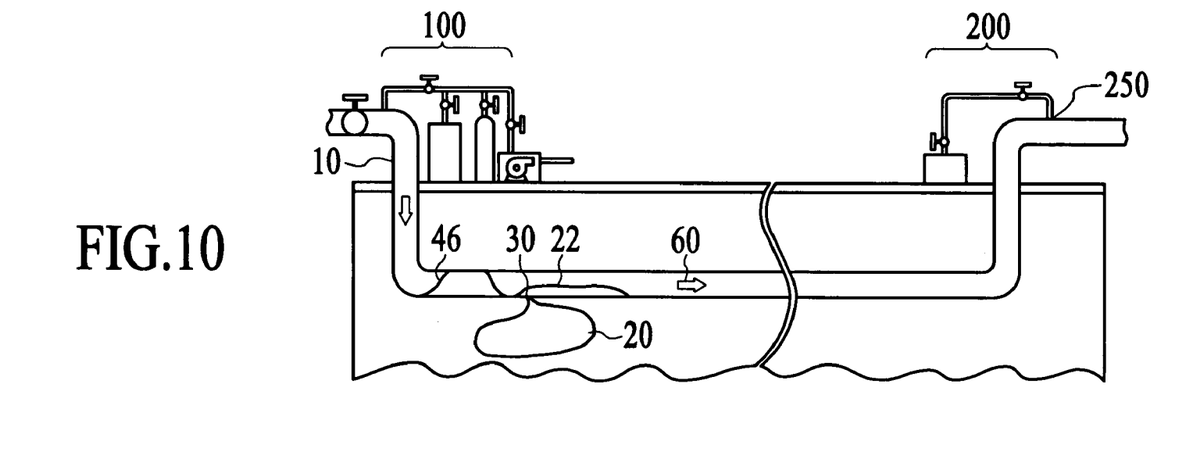
FIG. 10 is a simplified illustration of the method of the present invention for locating a hole in an underground pipe illustrated in FIG. 9 as the "slug" of tracer is being advected along the pipe towards the measurement location.
Figure 11:
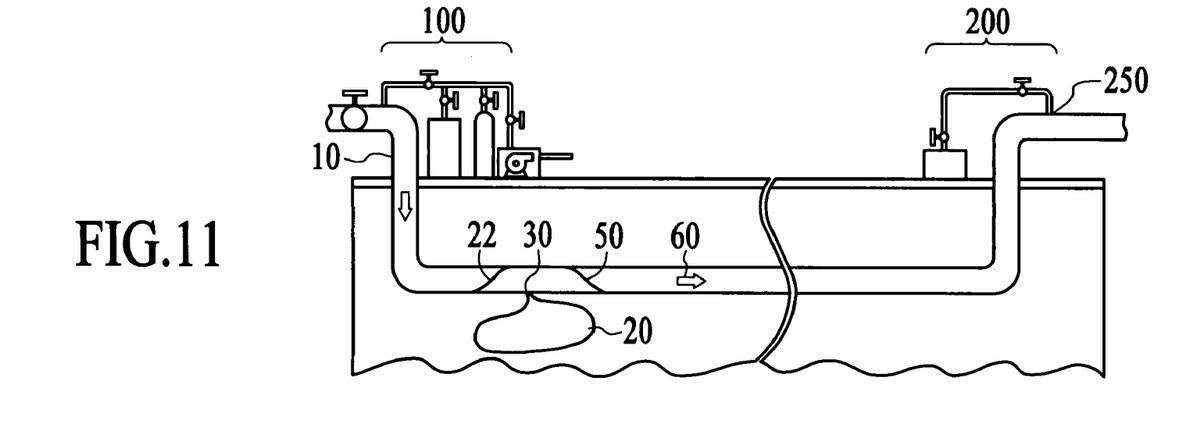
FIG. 11 is a simplified illustration of the method of the present invention for locating a hole in an underground pipe illustrated in FIG. 10 as the tracers have reached and interacted with the released material pulled back into the hole in the pipe. For determining the location of the hole, the pipe is rapidly flushed with an inert gas, as illustrated in FIG. 6, and then, as illustrated in FIG. 7, after the advection flow stream of the inert gas is reduced to a known velocity, the tracer being eluted back into the flow stream from the released material pulled back into the pipe, is transported to the measurement point at a known velocity.

For detection and location, the method requires the injection of a slug of partitioning tracer 44 upstream of the hole, as illustrated in FIG. 9. Then, as illustrated in FIG. 10, tracer slug 46 is transported at a known velocity 60 with an inert gas that does not interact with either the tracers or the contaminant to be located to a monitoring location 250 downstream of the hole 30. The partitioning tracer is selected so that when it passes by the liquid contaminant on the bottom of the pipe in the region of the holes it partitions into the contaminant as it passes by the hole. If detection is required, then the test continues until the lower magnitude or the longer time of arrival of the partitioning tracer compared to the conservative tracer is determined at the measurement point. For location, however, as illustrated in FIG. 6, the pipe must be flushed with an inert gas (i.e., the advection gas) of all the tracer in the pipe once the slug of partitioning tracers have passed this hole region. Then, as illustrated in FIG. 11, the velocity of the inert gas is adjusted to a known rate 60 to transport the tracer 50 that partitioned into the contaminant during the first pass and is now partitioning out of the contaminant and re-entering the advection flow stream. The location of the hole 30 is then determined from the time of arrival of the tracer coming out of the contamination and reaching the monitoring point 250.

Second Alternative Embodiment

The same approach will work if the pipe contains a liquid and the liquid is not removed from the pipe before the location measurement is made provided that the pipe is underground, the liquid contents are immiscible with water, and the hole is located beneath the groundwater table. In this case, groundwater is pulled back into the pipe when the vacuum is drawn on the pipe. The advection velocity is selected so that the fuel or water will be transported to a measurement point. The location of the hole is determined from the time of arrival of the water at the measurement point.

Third Alternative Embodiment

The water-tracer approach, described as an alternative embodiment of the second alternative embodiment, will also work if the pipe contains a gas that is not emptied before the location test is initiated provided that the chemical properties of this gas can be distinguished from the air pulled back into the line. In this case, the tracer is air, and the pipe can be located underground or aboveground.

This approach can also be used if the pipe is in a location in which another tracer gas besides air, such as helium, can be supplied to the environment surrounding the pipe. This is accomplished for an underground pipe by filling the pipe with helium under pressure so that the helium will be released into the soil and backfill surrounding the pipe in the immediate vicinity of the hole. Then the line is flushed to remove the helium gas. Once the helium gas has been removed from the line, the line is placed under a vacuum using the vacuum pump and any helium gas in the soil or backfill in the vicinity of the hole is pulled back into the line and then is transported at a known velocity using another inert gas (such as nitrogen) that can be distinguished from helium. For a pipe in which access to the outside surroundings of the pipe is possible, the helium gas can be placed in the environment directly. In this instance, helium does not need to be placed in the pipe. This application of the method works for pipe that may be located in a room or building, or the pipe in the inner pipe of a double-walled pipe.

What is claimed is:

1. A method for locating a hole in a fluid flow system, comprising the steps of:
   (a) injecting at a first location an interactive tracer into a fluid flow system containing the hole;
   (b) drawing a small vacuum on the fluid flow system to pull in any of the liquid or gas contents released from the pipe in the immediately vicinity of the hole;
   (c) removing the vacuum to allow the contents pulled back into the fluid flow system to remain in the approximate vicinity of the hole;
   (d) allowing the tracer sufficient time to interact with the contents pulled back into the fluid flow system;
   (e) advecting the tracer along the flow establishing an advection flow field;
   (c) extracting the tracer at a second location in the flow system;
   (d) measuring the concentration of the extracted tracer over a period of time; and
   (f) locating the hole from the measured tracer concentration.

2. The method of claim 1 wherein the hole is located from the time of arrival of the tracer as determined from the tracer concentration measurements.

3. The method of claim 1 wherein the presence of the hole is detected from the measured tracer concentration.

4. The method of claim 3 wherein the hole is detected from a reduction in amplitude of the tracer as determined from the tracer concentration measurements.

5. The method of claim 1 wherein the interactive tracer is a partitioning tracer.

6. The method of claim 1 wherein the interactive tracer is a reactive tracer.

7. The method of claim 5 further comprising the step of removing all of the tracer from the pipe before establishing the advection flow field in step (e).

8. The method of claim 1 wherein a hole signal is produced by introducing a detectable fluid into the fluid flow system so that it can leak out of the hole when the fluid flow system is pressurized, comprising the following steps prior to step (a):
   (i) introducing a target fluid that is detectable with a tracer into the fluid flow system;
   (ii) pressurizing the fluid flow system so that the target fluid will escape through the hole in the fluid flow system; and
   (iii) depressuring the fluid flow system so that step (a) can begin.

9. The method of claim 8 wherein the interactive tracer is a partitioning tracer that will partition into the target fluid.

10. The method of claim 1 wherein the tracer is injected only over a limited portion of the region to be interrogated.

11. The method of claim 1 where the injected tracer is advected at an approximately known flow rate throughout the fluid flow system with the hole.

12. The method of claim 1 wherein the injected tracer is advected at an approximately known speed throughout the fluid flow system with the hole.

13. The method of claim 1 wherein a plurality of tracers are injected.

14. The method of claim 1 wherein a plurality of interactive tracers are injected.

15. The method of claim 1 wherein the tracer is advected by a fluid that does not interact with the contents brought back into the fluid flow system through the hole.

16. The method of claim 1 wherein the tracer is advected by a fluid that does not interact with the tracers or the contents brought back into the fluid flow system through the hole.

17. The method of claim 1 wherein the distance from the hole to the second location is determined from the time of arrival of the partitioning tracer after said advection flow field has been re-established.

18. The method of claim 1 wherein the mean time of arrival is determined from a first arrival of the tracer at the second location.

19. The method of claim 1 wherein the mean time of arrival is determined from the leading edge of the measured concentration curve at the second location.

20. The method of claim 19 wherein the mean time of arrival is computed using the centroid of the measured concentration curves.

21. A method for determining the location of a hole in a fluid flow system, comprising the steps of:
   (a) drawing a small vacuum on the fluid flow system to pull in any of the liquid or gas contents released from the fluid flow system in the immediately vicinity of the hole;
   (b) removing the vacuum to allow the contents pulled back into the fluid flow system to remain in the approximate vicinity of the hole;
   (c) injecting a conservative tracer and a partitioning tracer into the flow system at a first location;
   (d) advecting the tracers along the flow system at a first advection speed to create an advection flow field;

(e) extracting the tracers at a second location in the flow system;
(f) measuring the concentration of the partitioning tracer as a function of the time until sufficient concentration data are collected so that the presence of the hole contents is detected;
(g) introducing a perturbation to the advection flow field at a perturbation time by changing and then re-establishing the advection flow at a second advection speed, which may be different than the first advection speed, creating a unique change in the concentration of the partitioning tracer;
(h) extracting at an extraction point the partitioning tracer as a function of time relative to the perturbation time;
(i) measuring the concentration of the partitioning tracer as a function of the time; and
(j) determining the location of contamination from the time of arrival of the partitioning tracer relative to the perturbation time and the advection flow speed.

22. The method of claim 21 where detection of the presence of the fluid flow system contents in the vicinity of the hole is determined from the presence of the interactive tracer that is being emitted from the fluid flow system contents after the tracers originally injected into the fluid flow system have been removed.

23. The method of claim 21 wherein the distance from the contaminant to the extraction point is determined from the time of arrival of the partitioning tracer after said advection flow field has been re-established.

24. The method of claim 23 wherein the mean time of arrival is determined from the first arrival of the tracer at the extraction point.

25. The method of claim 23 wherein the mean time of arrival is determined from the leading edge of the measured concentration curve at the extraction point.

26. The method of claim 21 wherein the distance from the contaminant to the extraction point is determined from the total distance between the first location and the extraction point and the ratio of the mean time of arrival of the partitioning tracer at the extraction point before and after re-establishing the advection flow field.

27. The method of claim 26 wherein the mean time of arrival is computed using the centroid of the measured concentration curves.

28. The method of claim 21 wherein a plurality of conservative and interactive tracers are injected.

29. The method of claim 1 wherein the contents of the fluid flow system are immiscible.

* * * * *